(12) United States Patent
Seyfried et al.

(10) Patent No.: US 10,520,434 B2
(45) Date of Patent: Dec. 31, 2019

(54) FLUORESCENCE LIFETIME IMAGING MICROSCOPY METHOD HAVING TIME-CORRELATED SINGLE-PHOTON COUNTING, WHICH METHOD PERMITS HIGHER LIGHT INTENSITIES

(71) Applicant: LEICA MICROSYSTEMS CMS GMBH, Wetzlar (DE)

(72) Inventors: Volker Seyfried, Nussloch (DE); Bernd Widzgowski, Dossenheim (DE); Frank Hecht, Mannheim (DE)

(73) Assignee: LEICA MICROSYSTEMS CMS GMBH, Wetzlar (DE)

( * ) Notice: Subject to any disclaimer, the term of this patent is extended or adjusted under 35 U.S.C. 154(b) by 0 days.

(21) Appl. No.: 16/304,168

(22) PCT Filed: May 24, 2017

(86) PCT No.: PCT/EP2017/062656
§ 371 (c)(1),
(2) Date: Feb. 27, 2019

(87) PCT Pub. No.: WO2017/202980
PCT Pub. Date: Nov. 30, 2017

(65) Prior Publication Data
US 2019/0339201 A1    Nov. 7, 2019

(30) Foreign Application Priority Data
May 25, 2016   (DE) .................. 10 2016 109 723

(51) Int. Cl.
*G01N 21/64* (2006.01)
(52) U.S. Cl.
CPC ..... *G01N 21/6408* (2013.01); *G01N 21/6458* (2013.01)

(58) Field of Classification Search
CPC .......... G01N 21/6408; G01N 21/6428; G01N 21/6458
See application file for complete search history.

(56) References Cited

U.S. PATENT DOCUMENTS 7,215,421 B2    5/2007    Kotani
7,999,238 B2    8/2011    Wolleschensky et al.
(Continued)

FOREIGN PATENT DOCUMENTS

DE          4339784 A1    5/1995
DE      102011052334 A1    2/2013
(Continued)

OTHER PUBLICATIONS

Michael Wahl: "The Principle of Time-Correlated Single Photon Counting", PicoQuant Technical Note, Jun. 24, 2014 (Jun. 24, 2014), pp. 1-14, XP055135297.
(Continued)

*Primary Examiner* — Yara B Green
(74) *Attorney, Agent, or Firm* — Leydig, Voit & Mayer, Ltd.

(57) ABSTRACT

A fluorescence lifetime imaging microscopy method with time-correlated single photon counting includes periodically exciting a sample to emit fluorescence photons, with a measurement interval being defined between each two successive excitation light pulses. A value characterizing fluorescence decay behavior is determined based on detection times of detected fluorescence photons, and imaging is performed based one the value. An analog detector signal is sampled within a plurality of sampling intervals within a respective one of the measurement intervals and is converted into a sequence of discrete signal values associated with the sampling intervals. It is determined based thereon whether more than a predefined number of fluorescence photons has been detected within the respective measurement interval. If
(Continued)

more than the predefined number of fluorescence photons has been detected, the respective measurement interval is discarded in the step of determining the value characterizing the fluorescence decay behavior.

21 Claims, 8 Drawing Sheets

(56) References Cited

U.S. PATENT DOCUMENTS

| | | |
|---|---|---|
| 10,073,034 B2 | 9/2018 | Widzgowski |
| 2013/0032699 A1 | 2/2013 | Widzgowski |
| 2013/0140437 A1 | 6/2013 | Widzgowski |

FOREIGN PATENT DOCUMENTS

| | | |
|---|---|---|
| DE | 102011055330 A1 | 5/2013 |
| DE | 102011055945 A1 | 6/2013 |
| WO | WO 2010089363 A1 | 8/2010 |

OTHER PUBLICATIONS

Jochen Arlt et al: "A study of pile-up in integrated time-correlated single photon counting systems", Review of Scientific Instruments., vol. 84, No. 10, Oct. 10, 2013 (Oct. 10, 2013), p. 103105, XP055278177.
Sebastian Isbaner et al: "Dead-time correlation of fluorescence lifetime measurements and fluorescence lifetime imaging", Optics Express, vol. 24, No. 9, Apr. 21, 2016 (Apr. 26, 2016), pp. 9429-9445, XP055396466.

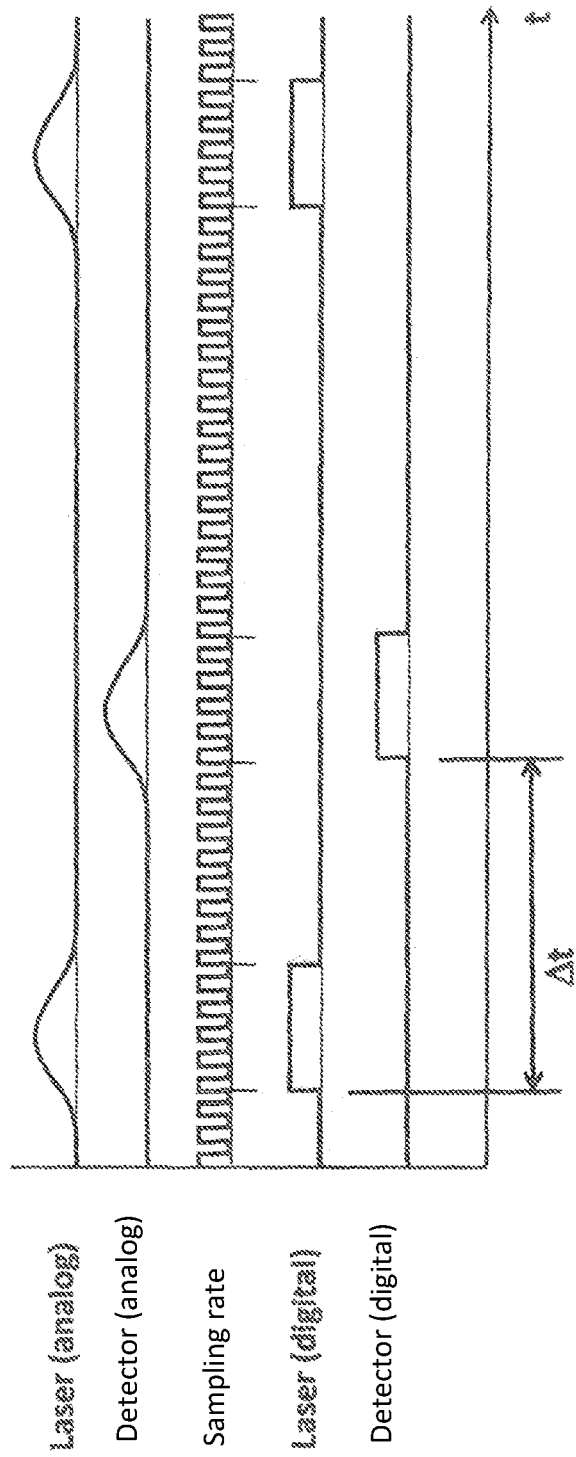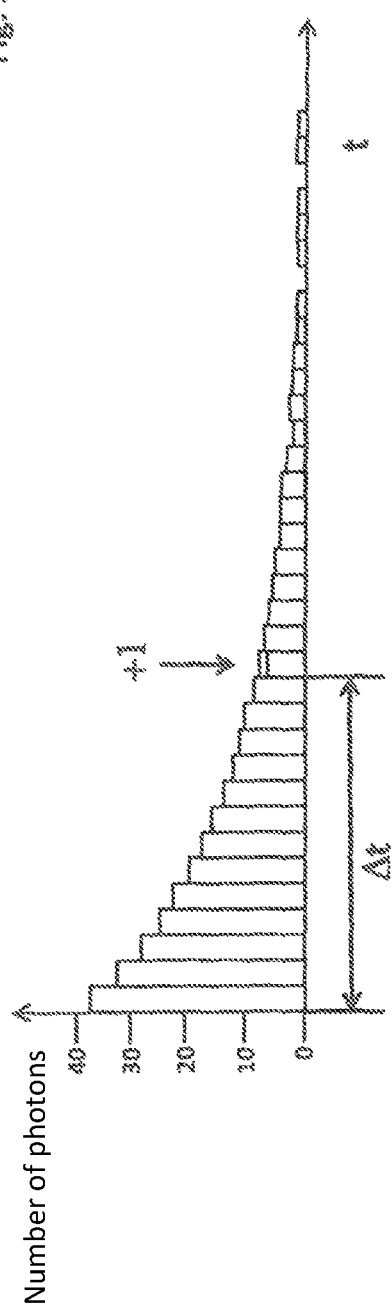

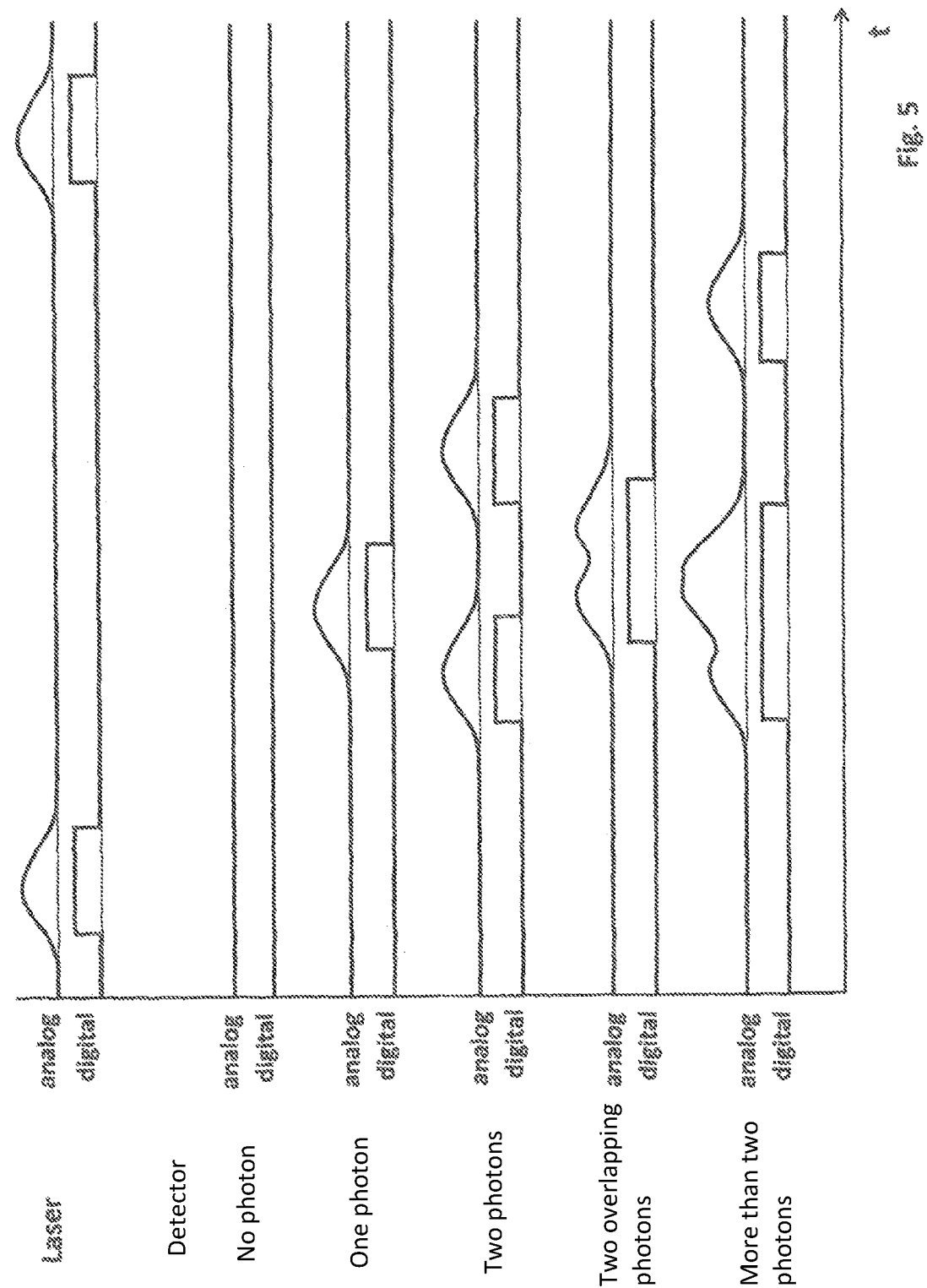

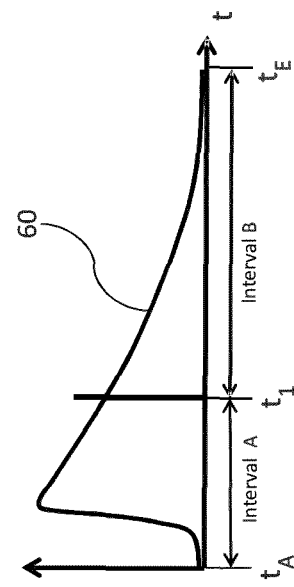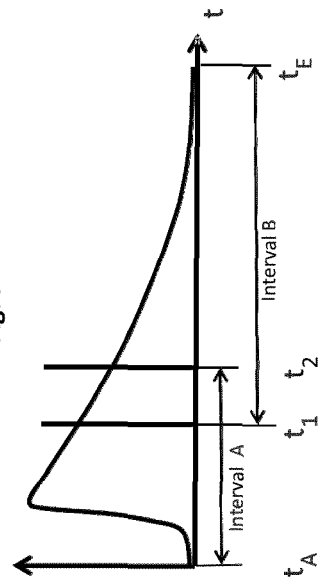

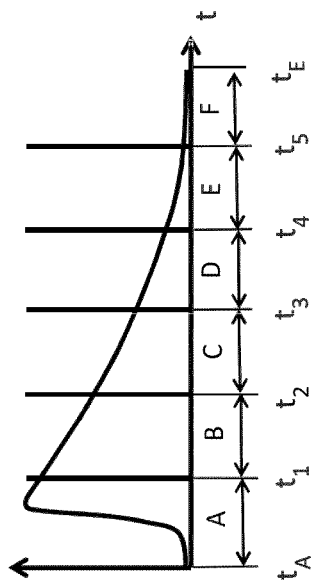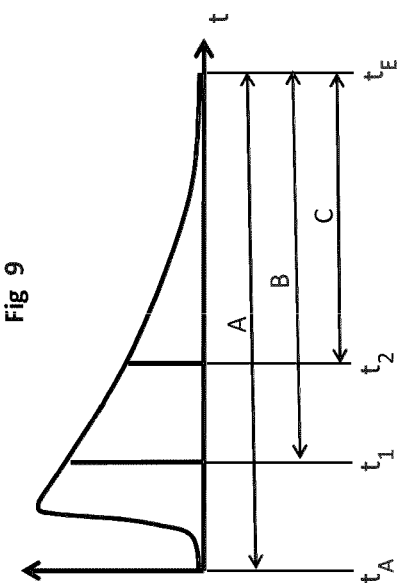

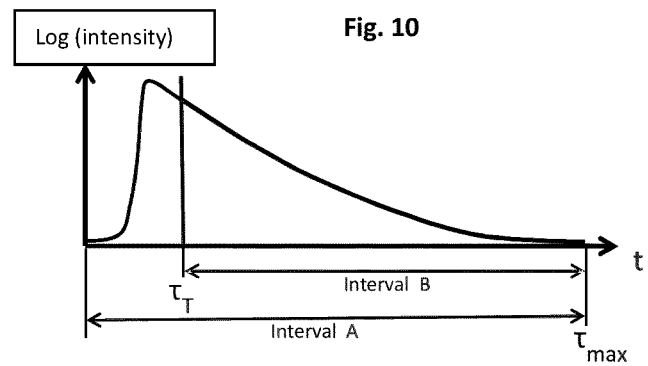
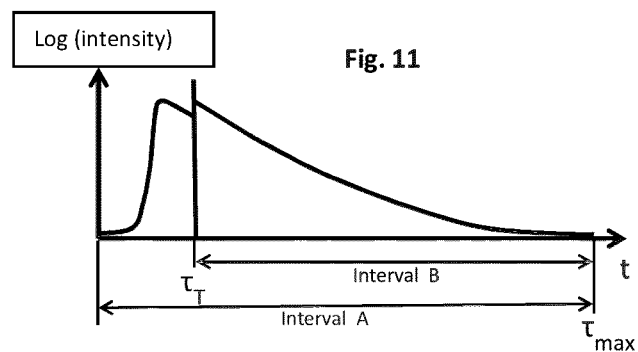
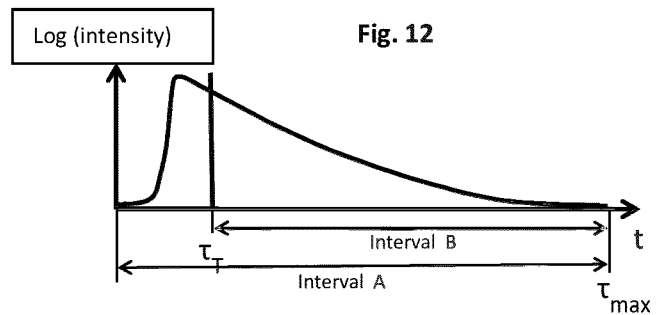

FLUORESCENCE LIFETIME IMAGING MICROSCOPY METHOD HAVING TIME-CORRELATED SINGLE-PHOTON COUNTING, WHICH METHOD PERMITS HIGHER LIGHT INTENSITIES

The invention relates to a fluorescence lifetime imaging microscopy method having time-correlated single photon counting according to the preamble of claim 1 and a microscope for carrying out such a method according to the preamble of claim 16.

Fluorescence lifetime imaging microscopy, abbreviated FLIM ("fluorescence lifetime imaging microscopy") is an imaging fluorescence microscopy method based on measurement of the different lifetimes of the excited states of fluorescent molecules. For example, the properties of the environment around the fluorescent molecules, such as the pH, temperature, ion concentration, FRET transitions (FRET="Förster resonance energy transfer"), etc., can be deduced on the basis of the measured lifetimes.

The fluorescence lifetime can be determined directly in the time domain ("time domain lifetime measurement") or in an alternative method in the frequency domain ("frequency domain lifetime measurement"). A determination in the time domain can be performed according to the so-called TCSPC ("time-correlated single photon counting") method. In this method the photons released by periodic excitation with excitation light pulses are detected individually. Accordingly, a detector that permits such single-photon detection is required for this purpose. The excitation light pulses used generally have a pulse period in the picosecond range, which is definitely shorter than a typical fluorescence lifetime in the nanosecond range. Typically the time between an excitation light pulse and the subsequent fluorescence signal detected by the detector is measured. The fluorescence photons detected in this way are then collected in a histogram based on numerous measurements. In such a histogram, the photon count is plotted as a function of the measured time. It is usually possible in this way to observe a time-dependent exponential decline in fluorescence intensity, which is represented by the single photons detected and from which the fluorescence lifetime is determined.

One problem with the method described above, which is based on single photon counting, is that conventional detectors are not ready to detect another photon for a certain period of time immediately after detecting a single photon. This period of time is also known as the dead time of the detector. A typical dead time of conventional detectors is in the range of approx. 50 to 100 ns. There is thus usually a restriction as regards the first fluorescence photon detected within relevant measurement interval defined between two successive excitation light pulses.

The shorter time slices may have a greater weight in the histogram because only the first fluorescence photon arriving after an excitation light pulse is taken into consideration. This greater weighting, which distorts the measurement result, is also called a pile-up effect among experts. To prevent this pile-up effect, the intensity of the incident excitation light pulses is typically adjusted so that only 1/10 photons per excitation light pulse is released. With this setting, the probability of detecting two fluorescence photons per excitation light pulse is approximately 1%. The pile-up effect can then be disregarded. However, such a great reduction in the excitation light intensity results in a correspondingly long detection time, which in turn stands in the way of wide-spread application of this method.

There are numerous approaches to solving the problem described above. First, parallelization of the electronic analyzer is proposed in the documents DE 10 2011 055 330 A1, DE 10 2011 055 945 A1 and DE 10 2011 052 334 A1, such that a digital data sequence derived from the detector signal is sent to a serial-parallel converter, which permits more rapid information processing of the data sequence. However, this parallelization of the electronic analyzer is technically complex and is therefore associated with a substantial cost.

WO 2010/089363 A1 proposes a numerical correction of the pile-up effect. However, this numerical correction presupposes a model of the expected results and therefore cannot be used universally.

DE 43 39 784 A1 discloses a time measurement device having a high time resolution. This device operates with a time-amplitude converter and a downstream analog-digital converter. The device is comparatively complex because of this converter configuration. The same is true of the time measurement device known from U.S. Pat. No. 7,999,238 B2, which uses a time-digital converter, whose the essential component is a cascade of comparators along a delay line.

Finally, with regard to the prior art, reference is made to U.S. Pat. No. 7,215,421 B2, which discloses a so-called time-gate method of fluorescence lifetime measurement. This method can be implemented with comparatively little equipment complexity but is subject to restrictions with regard to time resolution and signal yield. Time-gate methods that work with CCD or CMOS cameras have similar disadvantages.

It is the object of the present invention to provide a fluorescence lifetime imaging microscopy method as well as a microscope designed for implementing such a method, which will make it possible to increase the excitation light intensity with a comparatively low technical complexity while preventing a pile-up effect.

The present invention achieves this object by means of the subject matters of the dependent claims.

The present invention provides for a fluorescence lifetime imaging microscopy method with time-correlated single photon counting, in which a sample is excited periodically with excitation light pulses to emit fluorescence photons by means of a pulsed light source wherein a measurement interval between two successive excitation light pulses is defined, the fluorescence photons are detected by a detector, and an analog detector signal representing the detected fluorescence photons is generated, detection times at which the fluorescence photons are detected by the detector within the respective measurement intervals are determined on the basis of the detector signal, at least one value characterizing the fluorescence decay behavior is determined on the basis of the detection times of the detected fluorescence photons, and imaging is performed on the basis of this characterizing value. According to the invention, the analog detector signal is sampled at several sampling intervals within the respective measurement interval and converted to a sequence of signal values associated with the individual sampling intervals. There is a determination of whether more than a predefined number of fluorescence photons have been detected within the measurement interval based on the sequence of discrete signal values belonging to the respective measurement interval. This measurement interval is discarded for purposes of determining the value characterizing the fluorescence decay behavior if more than this predefined number of fluorescence photons has been detected, the predefined number being equal to or greater than 1.

The present invention thus proposes a subdivision of the respective defined measurement interval between two successive excitation light pulses into several sampling intervals in which the analog detector signal supplied by the detector is digitized. The sampling intervals here are significantly smaller than the expected fluorescence decay time. This digitization of the detector signal offers the possibility of subjecting the detector signal to a pattern recognition, i.e., to identify signal segments within the detector signal that are associated with one or more photons. It is then possible to determine on the basis of these detected signal segments whether more than a predefined number of fluorescence photons have been detected by the detector in the measurement interval in question. If this is the case, then this measurement interval is not taken into account for determining the value characterizing the fluorescence decay behavior. The predetermined photon count is selected by taking into account the dead time of the detector used, thereby reliably preventing a pile-up effect. This number is preferably equal to one, i.e., as soon as two, three or more photons have been identified on the basis of pattern recognition within the measurement interval in question, this measurement interval is discarded for purposes of determination of the characterizing value.

The measurement interval defined between two successive light pulses is not necessarily equal to the time interval between these two pulses. It is thus also conceivable to have the measurement interval begin only a short period of time after the first one of the two aforementioned excitation light pulses.

The value characterizing the fluorescence decay behavior is a fluorescence decay time, which can, for example, be derived from an exponential fluorescence decay curve obtained by means of a histogram. However, the aforementioned characterizing value is not limited to such a decay time. For example, it is possible to obtain the characterizing value by adding numerous exponential fluorescence decay curves and thus taking into numerous fluorescence decay times into account. The aforementioned variable can also be represented by the fluorescence decay curve itself.

The inventive step of discarding measurement intervals in which, e.g., more than one fluorescence photon is detected makes it possible to increase the excitation light intensity, while at simultaneously avoiding an unwanted pile-up effect. As mentioned in the introduction, comparable conventional methods aimed at preventing the pile-up effect typically work with excitation light intensities selected so that only 1/10 of the fluorescence photons are detected per excitation light pulse, which corresponds to a yield of 10%. On the other hand, with the method according to the invention, it is possible to work with an optimum light intensity, which results in one photon per measurement interval. Assuming a Poisson distribution of the fluorescence photons, the probability of the presence of x photons when n photons are expected is equal to $$P_n(x) = n^x/x! \cdot e^{-n}.$$

Consequently, for x=1, this yields the maximum number of photons per excitation light pulse as:

$$P_n(1) = \max \text{ for } n=1 \text{ at } P_1(1) = 37\%.$$

If this value is compared with the usual 10% yield, the result is an increase by a factor of 3.7.

The analog detector signal is preferably digitized by an analog-digital converter. In this way, the analog detector signal can be easily converted into a series of discrete signal values, which can in turn be supplied to pattern recognition according to the invention.

The analog detector signal is alternatively digitized by a comparator using a threshold value, so that each discrete signal values are equal to a first binary value or a second binary value. In this embodiment of the method according to the invention, the signal values of the data stream generated by digitizing the analog detector signal may assume only two values, e.g., 0 or 1, thus simplifying the pattern recognition.

Within the sequence of discrete signal values associated with the respective measurement interval, a partial sequence of signal values, all of which are equal to the first binary value, is defined as a photon interval, and the existence of more than one fluorescence photon within the measurement interval is ascertained if the number of sampling intervals present in the photon interval exceeds a predetermined sampling interval number. This definition of a photon interval makes it possible to ascertain in a particularly simple manner whether more than one photon has been detected within the observed measurement interval, and optionally, whether to discard this measurement interval for the determination of the value characterizing the fluorescence decay behavior.

Within a measurement interval, the sampling interval that first has the first binary value, is preferably defined as the beginning of the photon interval, while the sampling interval that has the second binary value next is defined as the end of the photon interval, the aforementioned number being determined on the basis of the beginning and the end of the photon interval. In this embodiment, pattern recognition according to the invention is thus reduced to determining the first sampling interval, e.g. with a value of 1 as the start of the photon interval, and determining the first sampling interval with a value of 0 as the end of the photon interval.

In a particularly preferred embodiment, the intensity of the excitation light pulses for a predetermined pixel in a reference measurement is determined according to the following equation:

$$I_{ex}(x,y) = I \cdot N(x,y,0)/N(x,y,1)$$

where
I denotes the intensity in the reference measurement,
$I_{ex}$ denotes the intensity to be determined,
N(x, y, k) denotes the total number of measurement intervals in which k=1 or k=0 fluorescence photons have been detected, and
(x, y) denotes the location of the pixel.

The intensity of the excitation light pulse can preferably be adjusted for the predetermined pixel so that the total number of measurement intervals in which exactly one fluorescence photon is detected is equal to the total number of measurement intervals in which no fluorescence photon is detected.

The microscopy method according to the invention is preferably implemented by using a confocal scanning microscope or a multiphoton microscope. Both a confocal scanning microscope and a multiphoton microscope are thus significant components of the instrument technology required to carry out the method according to the invention, in particular a pulsed laser light source.

A particularly preferred embodiment provides for application of the method outlined above, not to the entire measurement interval, but instead to various segments of the interval, which are defined within the measurement interval. This further embodiment can thus be regarded as an expansion of the basic method, which is based only on the entire measurement interval. In this expansion of the basic method, various interval segments within the respective measurement interval are defined, wherein the determination of whether more than the predefined number of fluorescence photons has been detected within the measurement interval is carried out separately for each one of these interval segments. If more than the predefined number of fluorescence photons has been detected within the interval segment in question, then this interval segment is discarded for determination of the value characterizing the fluorescence decay behavior. In this case, each interval segment has a plurality of sampling intervals.

Due to the subdivision of the measurement interval into various interval segments as provided in this expansion of the basic method, the photon yield can be increased substantially. The definition of various interval segments according to the invention is to be understood to mean that one of these interval segments may also be the measurement interval per se.

The value characterizing the fluorescence decay behavior is preferably determined for each interval segment of the respective measurement interval, and the characterizing value based on the total measurement interval is determined from the characterizing values determined for the individual interval segments. For example, if the value characterizing the fluorescence decay behavior is given by a fluorescence decay curve, then the fluorescence decay curves, which are based on the various interval segments and are each also referred to as segmental decay curves, are, in this embodiment, combined into an overall decay curve based on the total measurement interval.

The characterizing value based on the total measurement interval is preferably ascertained on the basis of a factor determined from the number of interval segments in which the predefined number of fluorescence photons has been detected, and from the number of interval segments in which no photon has been detected. This factor ensures in particular that the decay curves determined separately for the individual interval segments can be combined to yield a continuous overall decay curve, which is then to be input for further analysis.

The characterizing value based on the total measurement interval is preferably analyzed on the basis of a model function, in which the number of fluorescence photons detected in the interval segments is taken into account. Then the aforementioned model function can be selected properly by taking the photon statistics on which the method is based into account.

In another embodiment, the various interval segments each comprise at least two segments, which are immediately connected to each other with or without a time overlap within the measurement interval.

In an alternative embodiment, the various interval segments comprise a first segment, which is given by the measurement interval, and at least one second segment whose start is delayed with respect to the beginning of the measurement interval and whose end coincides with the end of the measurement interval. In this embodiment, the interval segments can be staggered, so that the yield of fluorescence photons can be increased.

According to another aspect of the invention, a microscope is provided for performing fluorescence lifetime imaging microscopy with time-correlated single photon counting according to the subordinate claim 16.

The microscope for performing fluorescence lifetime imaging microscopy with time-correlated single photon counting accordingly comprises a light source, a detector and a processing unit. The light source is designed to excite a sample with excitation light pulses to emit fluorescence photons. A measurement interval is defined between two successive excitation light pulses. The detector is designed to detect the fluorescence photons and to generate the analog detector signal representing the detected fluorescence photons. The processing unit is designed to determine, on the basis of the detector signal, the detection times at which the fluorescence photons are detected by the detector within the respective measurement intervals, then to determine, on the basis of the detection times of the detected fluorescence photons, at least one value characterizing the fluorescence decay behavior, and to perform imaging on the basis of the characterizing value. According to the invention, the processing unit is designed to sample the analog detector signal within the respective measurement interval in several sampling intervals and convert it into a sequence of discrete signal values associated with the individual sampling intervals. The processing unit is designed to determine, on the basis of the sequence of discrete signal values associated with the respective measurement interval, whether more than a predefined number of fluorescence photons has been detected within the measurement interval, and to then discard this measurement interval for the determination of the value characterizing the fluorescence decay behavior if more than this predefined number of fluorescence photons has been detected, the predefined number being equal to or greater than 1.

The processing unit preferably comprises an analog-digital converter designed to digitize the analog detector signal. The processing unit may comprise a comparator designed to digitize the analog detector signal by using a threshold value, so that the discrete signal values are each equal to a first binary value or to a second binary value.

In a preferred embodiment of the microscope according to the invention, another detector is also provided in addition to the detector intended for detecting the fluorescence photons, and is designed to detect the excitation light pulses and to generate an analog excitation signal representing the detected excitation light pulses, wherein the processing unit is designed to scan the analog excitation signal in accordance with the sampling intervals and to convert it to a sequence of discrete excitation signal values associated with the individual sampling intervals. This sequence of discrete excitation signal values forms a data stream that is used to define the measurement intervals and thus as a reference for the detection times determined of the fluorescence photons.

The processing unit preferably comprises a display device for displaying the setting information. It is possible to offer the user aids that enable him to optimally adjust the microscope and/or the operation of the processing unit using the setting information displayed on the display device. The user can, for example, be made aware of the average number of fluorescence photons in the measurement interval. In doing so, the average number of photons may be based on the entire image capture area or only on a part thereof. The setting information may be displayed to the user in the form of numbers and/or in the form of a graphical representation. For image capture at only one sample site, the setting information may, for example, be displayed in the form of two bar symbols, e.g. showing the number of measurement intervals without a fluorescence photon and the number of measurement intervals with a single fluorescence photon. The user can then set the excitation light intensity so that both bar symbols on the display device are of the same length.

The invention is illustrated in greater detail below on the basis of the figures, in which:

FIG. 3 shows a diagram showing the laser signals and detector signals generated on the basis of an example, in which exactly one fluorescence photon is detected within the measurement interval in question;

FIG. 4 shows a histogram based on the example according to FIG. 3;

FIG. 5 shows a diagram illustrating other examples of laser signals and detector signals;

FIGS. 6 through 9 show diagrams illustrating the various examples of segmentation of the measurement interval; and FIGS. 10 through 13 show diagrams illustrating how segmented fluorescence decay curves are adapted to one another.

FIG. 1 shows a confocal scanning microscope 10, which represents an example embodiment of the microscope according to the invention.

Figure 1:
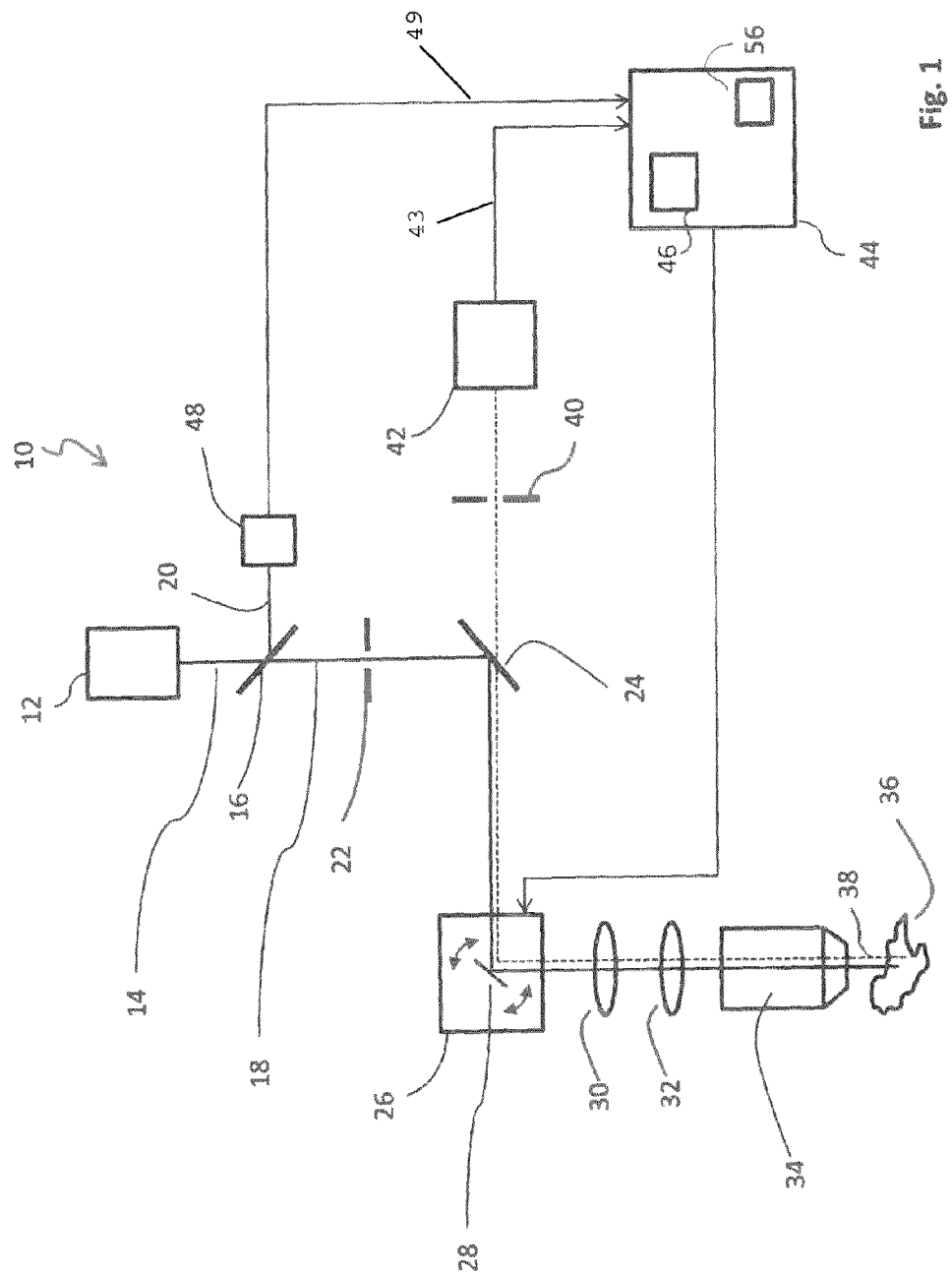
FIG. 1 shows a confocal scanning microscope representing an embodiment of the microscope according to the invention.

The confocal scanning microscope 10 has a pulsed laser light source 12 designed to emit light with periodic excitation light pulses. The excitation light labeled as 14 in FIG. 1 falls onto a beam splitter 16, which splits the excitation light 14 into a transmitted component 18 and a reflected component 20.

The excitation light 18 transmitted through the beam splitter 16 passes through an excitation aperture 22 and is then reflected by a dichroic beam splitter 24 in the direction of a scanning unit 26. The scanning unit 26 includes a gimbaled scanning mirror 28, and reflects the excitation light 14 in the direction of a scanning lens 30. After passing through the scanning lens 30 and a tube lens 32, the excitation light enters a microscope objective 34, which directs the excitation light 18 onto a sample 36.

Fluorescent molecules are excited to emit fluorescent light 38 in the area of the sample 36 illuminated by the excitation light 18. Fluorescence photons constituting fluorescent light 38 propagate along the light path along which the excitation signal 18 enters the sample 36, starting from the beam splitter 24, and then goes back to the beam splitter 24 in the reverse direction. After passing through the beam splitter 24 and a detection aperture 40, the fluorescent light reaches a first detector 42. The first detector 42 converts the received fluorescent light 38 into an analog detector signal 43, which is then sent to a processing unit 44. The processing unit 44 is designed to scan the analog detector signal 43 in a predetermined sampling cycle and thereby convert the analog detector signal 43 into a digital detector signal. This digital detector signal constitutes a sequence of discrete signal values associated with individual sampling intervals corresponding to the sampling cycle. The processing unit 44 includes a comparator 46 for the purpose of sampling the analog detector signal 43. An analog-digital converter may also be provided instead of the comparator 46.

In addition to the first detector 42, which converts the received fluorescent light 38 into the analog detector signal, the scanning microscope 10 has a second detector 48 located in the beam path diverted by the beam splitter 16. The second detector 48 therefore receives the portion 20 of the excitation light 14 emitted by the laser light source 12 and reflected by the beam splitter 16. The second detector 48 converts the portion of the excitation light 20 reflected on the beam splitter 16 into an analog excitation signal 49 and supplies it to the processing unit 44. The processing unit 44 samples the analog excitation signal 49 sent to it at the predetermined sampling rate and thus converts the analog excitation signal 49 into a digital signal consisting of a sequence of discrete excitation signal values associated with the individual sampling intervals. To accomplish this, the processing unit 44 again has a comparator or an analog-digital converter, which is not shown explicitly in FIG. 1. The analog excitation signal 49 supplied by the second detector 48 and the digital signal generated therefrom by the processing unit 44 are hereinafter referred to as the analog and digital laser signals, respectively.

The processing unit 44 is also designed to control the scanning unit 28 in an essentially known manner. The processing unit 44 furthermore has a display device 56, for example, a monitor.

In the context of the present invention, the processing unit 44 particularly has the job of determining the detection times at which the detector 42 receives the fluorescence photons emitted by the sample 36, from the analog detector signal 43 supplied by the detector 42. It is on the basis of these detection times that the processing unit 44 determines a value characterizing the fluorescence decay behavior, for example, a fluorescence decay time. To avoid the pile-up effect explained in the introduction, the processing unit 44 is designed according to the present invention to determine, on the basis of the digital detector signal, whether more than a predefined number of fluorescence photons have been detected by the detector 42 within a measurement interval e.g. defined by two successive excitation light pulses. If this is the case, the processing unit 44 excludes this measurement interval from the determination of the value characterizing the fluorescence decay behavior.

The role of the processing unit 44 described above is illustrated in the following discussion on the basis of the diagrams shown as an example in FIGS. 2 through 5. In doing so, it is additionally assumed that the processing unit 44 will exclude the measurement interval in question from the determination of the fluorescence decay behavior if the processing unit 44 ascertains that more than one fluorescence photon has been detected within this measurement interval.

Figure 2:
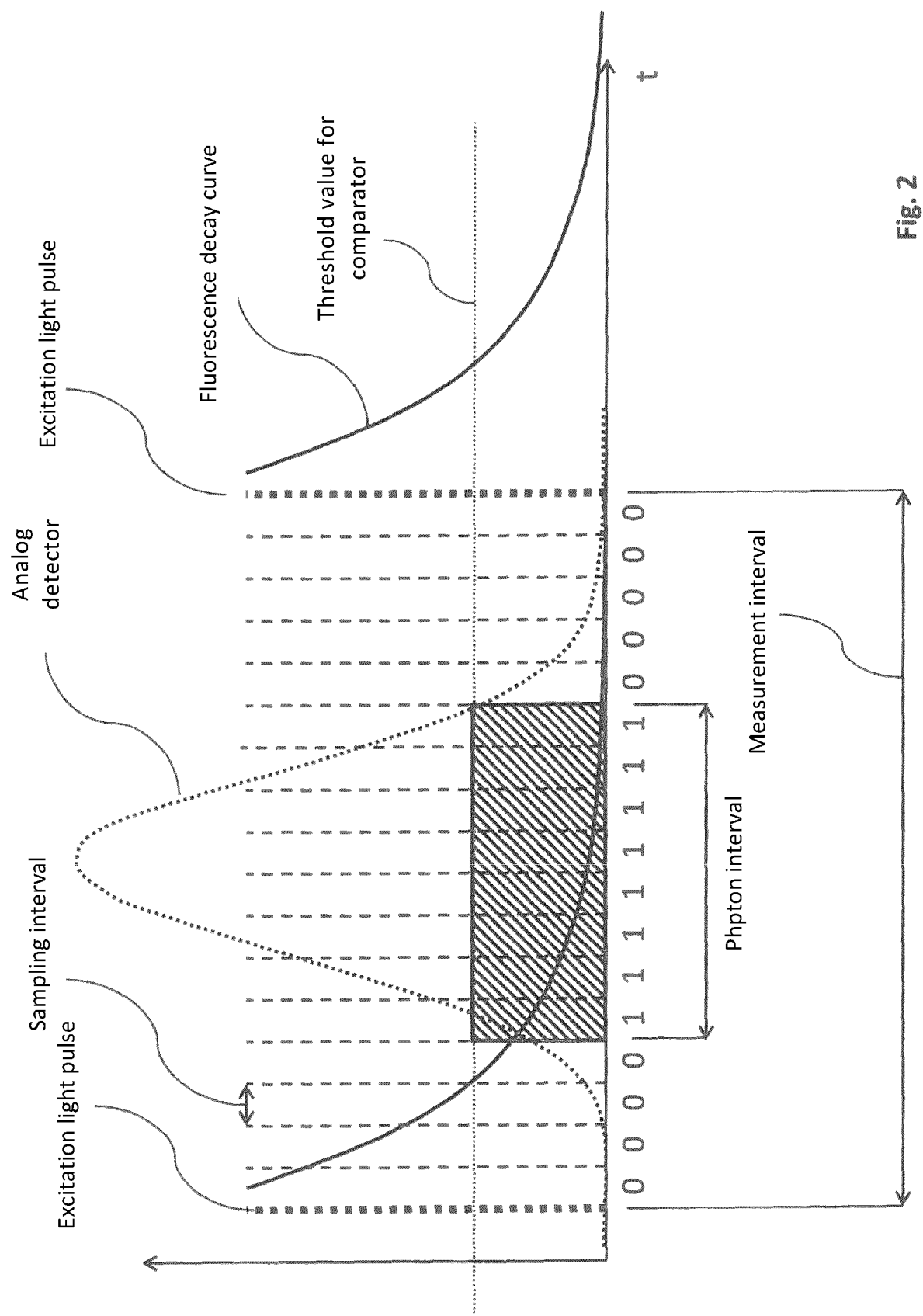
FIG. 2 shows a diagram illustrating the sampling of an analog detector signal according to the invention.

The diagram in FIG. 2 shows a defined measurement interval between two successive excitation light pulses within which the detector 42 detects a fluorescence photon and generates a corresponding analog detector signal 43. As also shown in FIG. 2, the measurement interval is subdivided into numerous sampling intervals by way of the sampling of the analog detector signal 43 performed by the processing unit 44. FIG. 2 also shows a threshold value used by the comparator 46, on the basis of which either the binary value 0 or the binary value 1 is associated with the analog detector signal in each sampling interval. If the analog detector signal in a sampling interval in question is less than or equal to the threshold value, then the binary value 0 is assigned to this sampling interval. However, if the digital detector signal in a sampling integral is greater than the threshold value, then the binary value 1 is assigned to this sampling interval. In the example according to FIG. 2, a subsequence of binary values 1, which define a photon interval, is thus obtained in a middle range of the measurement interval. Since exactly one fluorescence photon is detected in the measurement interval in question in the example shown in FIG. 2, this measurement interval is taken into account by the processing unit 44 in determining the fluorescence decay behavior.

FIG. 2 also shows a fluorescence decay curve to illustrate that the duration of the sampling intervals corresponding to the sampling cycle used by the signal processing unit 44 is much shorter than the fluorescence decay time.

For the case when exactly one fluorescence photon is detected within a measurement interval by the first detector 42, the diagram according to FIG. 3 shows the analog laser signal generated by the second detector 48, the digital laser signal generated therefrom by sampling via the signal processing unit 44, the analog detector signal generated by the first detector 42, the digital detector signal generated therefrom by the signal processing unit 44, and the sampling cycle used by the signal processing unit 44 for the purpose of signal sampling. As FIG. 3 also shows, the signal processing unit 44 determines the time at which the fluorescence photon is detected within the measurement interval in question by the detector 42 based on the rising flanks of the digital laser signal and the digital detector signal. The detection time is labeled Δt in this figure.

FIG. 4 shows an example of a histogram, which represents the result of numerous individual measurements, wherein the symbol "+1" in FIG. 4 is based on the measurement interval shown in FIG. 3. This shows the frequency of the individual measurements of detected photons, in which the measured detection time was t.

FIG. 5 illustrates a few examples progressions of respectively analog and digital laser signals, as well as respectively analog and digital detector signals. In the embodiment described above, only the case in which exactly one photon is detected on the basis of the detector signal within the measurement interval in question is taken into account in determining the fluorescence decay behavior and thus in supplementing a histogram of the type shown in FIG. 4. The measurement intervals in which two or more photons are in particular detected, are neglected in determining the value characterizing the fluorescence decay behavior.

An example embodiment of the method of this invention in which a measurement just being considered for determining the fluorescence decay behavior is discarded if the processing unit 44 determines that more than one fluorescence photon was captured was explained by referring to FIGS. 1 through 5. In this example embodiment, approx. 63% of the total number of fluorescence photons striking the detector 42 remains unused in determining the fluorescence decay behavior because measurement intervals with more than one fluorescence photon are discarded. Therefore, an enhancement of the basic method described above, which will make it possible to also use a portion of the fluorescence photons disregarded in the basic method for the analysis, is described below.

This enhancement of the invention provides for applying the basic method to various interval segments that are defined within the respective measurement interval. One example of such a segmentation of the measurement interval is illustrated in the diagram according to FIG. 6.

The measurement interval in FIG. 6 is defined between a starting time $t_A$ and an ending time $t_E$. In the segmentation according to FIG. 6, the measurement interval is subdivided into a first interval segment A and a second interval segment B. The interval segment A extends from starting time $t_A$ to time $t_1$. The interval segment B extends from time $t_1$ to ending time $t_E$. For the sake of illustration, FIG. 6 also shows a fluorescence decay curve 60 in the form of a histogram showing the results of numerous individual measurements (corresponding to FIGS. 2 and 4).

This enhancement of the invention provides for applying the basic method described previously separately to the two interval segments A and B. This means that, in the present example, a separate fluorescence decay curve characterizing the value the fluorescence decay behavior of the two interval segments A and B is determined. In doing so, only the interval segments A and/or B, in which the detected number of fluorescence photons does not exceed a predefined number, which should again be equal to 1 in the present example, are taken into account in the analysis. If the number of detected fluorescence photons in the respective interval segment A and/or B is greater than 1, then the latter is discarded for purposes of determining the fluorescence decay curve.

This segmentation of the measurement interval into the two successive segment intervals A and B, as shown in FIG. 6, is to be understood as just an example. The measurement interval may thus also be segmented in a different way, as illustrated in FIGS. 7 through 9.

FIG. 7 shows a segmentation in which the two segment intervals A and B have a time overlap between the times $t_1$ and $t_2$. The interval segment A thus ends only at time $t_2$ which occurs after time $t_1$ at which interval segment B begins.

FIG. 8 shows a segmentation, in which the measurement interval is subdivided into more than two interval segments, e.g., six segments A through F. As in FIG. 6, the individual interval segments A through F in the segmentation according to FIG. 8 follow one another without a time overlap.

FIG. 9 shows a definition of three interval segments A, B and C, of which the interval segment A corresponds to the measurement interval, while the two other interval segments B and C have starting times $t_1$ and $t_2$ that are delayed in a staggered manner with respect to the starting time to of the interval segment A. The ending time $t_E$ is the same for all interval segments A, B and C.

The segmentations illustrated as examples in FIGS. 6 through 9 can also be combined with one another in a suitable manner. Thus, for example, the interval segments A through F, which follow one another without a time overlap in FIG. 8, overlap with one another in time as illustrated for the two interval segments A and B in FIG. 7.

It is explained below with reference to FIGS. 10 through 13 how the fluorescence decay curves determined separately for the individual interval segments are combined to yield an overall curve applying to the entire measurement interval. FIGS. 10 through 13 here are based purely as an example on a segmentation with two interval segments A and B, wherein the interval segment A is equal to the measurement interval, while the interval segment B shows an interval which is that in comparison with the measurement interval and whose starting point is delayed with respect to the starting point of the measurement interval. FIGS. 10 through 13 show the starting time of interval segment B as τr and the ending time shared by the two interval segments A and B as $\tau_{max}$.

In the example shown in FIGS. 10 through 13, a separate fluorescence decay curve is determined by analyzing numerous interval segments B according to the present expansion of the basic method. In doing so, only the interval segments B in which no more than a predefined number of photons, equal to 1 in the present example, is detected are taken into account in determining this segmental fluorescence decay curve. In this way, the total number of fluorescence photons detected in the interval segments B can be increased in comparison with the case where the basic method is applied only to the entire measurement interval.

Figure 13:
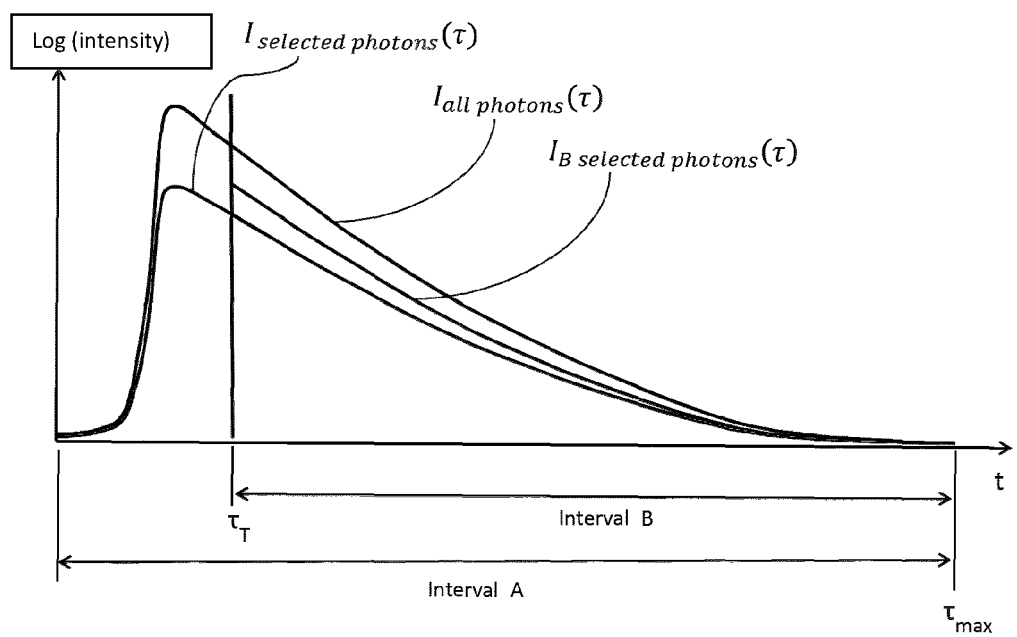

As shown in FIG. 11, determining the segmental fluorescence decay curve based on the interval segment B reveals a discontinuity in comparison with the portion of the fluorescence decay curve, which is based on the entire measurement interval and is situated outside of interval segment B. The extension of the basic idea therefore provides that, to eliminate this discontinuity, i.e., to adjust the segmental fluorescence decay curve based on the interval segment B to the portion of the fluorescence decay curve based on the entire measurement interval occurring at an earlier point in time, the intensities in the interval segment B are multiplied by a factor F in order to obtain a discontinuity-free, i.e., a smooth, fluorescence decay curve according to FIG. 12:

$$I(\tau) = \begin{cases} I_{selected\ photons}(\tau) & \text{for } \tau \leq \tau_T \\ F \cdot I_{B\ selected\ photons}(\tau) & \text{for } \tau > \tau_T \end{cases}$$

where $$F = \frac{\int_0^{\tau_{max}} I_{selected\ photons}(\tau)d\tau}{\int_0^{\tau_{max}} I_{all\ photons}(\tau)d\tau} \cdot \frac{\int_{\tau_T}^{\tau_{max}} I_{all\ photons}(\tau)d\tau}{\int_{\tau_T}^{\tau_{max}} I_{B\ selected\ photons}(\tau)d\tau}$$

where $I_{selected\ photons}(\tau)$ denotes the fluorescence decay curve determined by the basic method for the entire measurement interval, while $I_{B\ selected\ photons}(\tau)$ denotes the segmental fluorescence decay curve determined when the basic method is applied only to interval segment B. Furthermore, $I_{all\ photons}(\tau)$ denotes an idealized fluorescence decay curve that would result if the reception times for all the fluorescence photons were known. The aforementioned decay curves are illustrated in FIG. 13.

The function $I_{all\ photons}(\tau)$ cannot be determined accurately from the recorded data, but the integrals over the aforementioned functions are known from photon statistics:

$$\int_0^{\tau_{max}} I_{A\ selected\ photons}(\tau)d\tau = \frac{N_A(1)}{N_A(0)} \cdot e^{-\frac{N_A(1)}{N_A(0)}} \cdot \int_0^{\tau_{max}} I_{all\ photons}(\tau)d\tau$$

and $$\int_{\tau_T}^{\tau_{max}} I_{B\ selected\ photons}(\tau)d\tau = \frac{N_B(1)}{N_B(0)} \cdot e^{-\frac{N_B(1)}{N_B(0)}} \cdot \int_{\tau_T}^{\tau_{max}} I_{all\ photons}(\tau)d\tau$$

where $N_A(k)$ and $N_B(k)$ denote the number of measurement intervals in which k fluorescence photons have been detected in the interval segments A and/or B. The factor F is thus simplified as follows:

$$F = \frac{N_A(1)}{N_A(0)} \cdot \frac{N_B(0)}{N_B(1)} e^{\left(\frac{N_B(1)}{N_B(0)} - \frac{N_A(1)}{N_A(0)}\right)}$$

By taking the factor F into account, the smooth decay curve according to FIG. 12 is constructed from the segmented fluorescence decay curves shown in FIG. 11 with a discontinuity between them.

The fluorescence decay curve shown in FIG. 12 can then be determines by using a model function $f(\tau)$, which is applicable to the photon statistics in question and which displays an exponential decay with one or more components:

$$f(\tau) = \int_0^\tau IRF(x) \cdot \sum_{n=1}^m A_n \cdot e^{-\frac{\tau-x}{\tau_n}} dx$$

where m denotes the number of exponential components, $A_n$ denotes the amplitude of the respective component, $\tau_n$ denotes the fluorescence lifetime of the component and $IRF(\tau)$ denotes an instrument response function.

A method of nonlinear adjustment of the model function $f(\tau)$ to the fluorescence decay curve constructed according to FIG. 12 is, e.g. used to determine the fluorescence lifetime $\tau_n$. Such a method may, for example, be the minimization of a so-called maximum likelihood estimation function with Poisson statistics, such as that described by Z. Bajzer et al., "Maximum-Likelihood Method For the Analysis Of Time-Resolved Fluorescence Decay Curves," European Biophysics Journal, 1991, 20(5):247-262. If one proceeds in this way, the model function $f(\tau)$ and the constructed fluorescence decay curve $I(\tau)$ are modified according to the following procedure:

$$f' = \begin{cases} f(\tau) & \text{for } \tau \leq \tau_T \\ \dfrac{f(\tau)}{F} & \text{for } \tau > \tau_T \end{cases}$$

and $$f' = \begin{cases} f(\tau) & \text{for } \tau \leq \tau_T \\ \dfrac{f(\tau)}{F} & \text{for } \tau > \tau_T \end{cases}$$

The functions $f(\tau)$ and $I(\tau)$ modified in this way are then adapted to one another in a known way for further evaluation.

The expansion of the basic method above can also be used in cases in which the measurement interval is segmented in some other way than that illustrated in FIGS. 10 through 13. In particular, the photon yield can be increased permanently by dividing the measurement interval into numerous interval segments in which the method outlined above is employed. A particularly high photon yield is in particular obtained when a corresponding division of the measurement interval into M interval segments takes place when M time channels are recorded. In this case, an array of correction factors $F(\tau)$ is generated together with the constructed decay curve $I(\tau)$ and is made available for a more extensive analysis.

LIST OF REFERENCE NUMERALS

10 Confocal scanning microscope
12 Pulsed laser light source
14 Excitation light
16 Beam splitter
18 Transmitted excitation light
20 Reflected excitation light
22 Excitation aperture
24 Dichroic beam splitter
26 Scanning unit
28 Scanning mirror
30 Scanning lens
32 Tubular lens
34 Microscope objective
36 Sample
38 Fluorescent light
40 Detection aperture 42 First detector
43 Analog detector signal
44 Processing unit
46 Comparator or analog-digital converter
48 Second detector
49 Analog excitation signal
56 Display unit
60 Fluorescence decay curve

The invention claimed is:

1. A fluorescence lifetime imaging microscopy method with time-correlated single photon counting, the method comprising:
periodically exciting a sample to emit fluorescence photons using a pulsed light source emitting excitation light pulses, with a measurement interval being defined between each two successive excitation light pulses;
detecting the fluorescence photons using a detector and generating an analog detector signal representing the detected fluorescence photons, wherein detection times at which the fluorescence photons are detected by the detector within the respective measurement intervals are determined based on the analog detector signal;
determining at least one value characterizing fluorescence decay behavior based on the detection times; and
performing imaging based on the at least one value,
wherein the analog detector signal is sampled within a plurality of sampling intervals within a respective one of the measurement intervals and is converted into a sequence of discrete signal values associated with the sampling intervals, and it is determined based on the sequence of discrete signal values belonging to the respective measurement interval whether more than a predefined number of fluorescence photons greater than or equal to 1 has been detected within the respective measurement interval, and
wherein the respective measurement interval for which it has been determined that more than the predefined number of fluorescence photons has been detected is discarded in the step of determining the at least one value characterizing the fluorescence decay behavior.

2. The fluorescence lifetime imaging microscopy method according to claim 1, wherein the predefined number is equal to 1.

3. The fluorescence lifetime imaging microscopy method according to claim 1, wherein the analog detector signal is digitized by an analog-digital converter.

4. The fluorescence lifetime imaging microscopy method according to claim 1, wherein the analog detector signal is digitized by a comparator using a threshold value such that the discrete signal values are each equal to a first binary value or equal to a second binary value.

5. The fluorescence lifetime imaging microscopy method according to claim 4, wherein a partial sequence of the discrete signal values, all of which are equal to the first binary value, is defined as a photon interval within the sequence of discrete signal values associated with the respective measurement interval, and wherein presence of more than one fluorescence photon within the respective measurement interval is detected if the number of sampling intervals contained in the photon interval exceeds a predefined sampling interval number.

6. The fluorescence lifetime imaging microscopy method according to claim 5, wherein the sampling interval that is first to have the first binary value within the respective measurement interval is defined as the beginning of the photon interval, and the sampling interval that is next to have the second binary value is defined as the end of the photon interval, with the sampling interval number being determined based on the beginning and the end of the photon interval.

7. The fluorescence lifetime imaging microscopy method according to claim 1, wherein an intensity of the excitation light pulses for a predetermined pixel is determined in a reference measurement according to the following equation:

$$I_{ex}(x,y) = I \cdot N(x,y,0)/N(x,y,1)$$

where
I denotes an intensity in the reference measurement,
$I_{ex}$ denotes the intensity to be determined,
N(x, y, k) denotes the total number of measurement intervals, in which k=1 or k=0 fluorescence photons have been detected, and
(x, y) denotes the location of the pixel.

8. The fluorescence lifetime imaging microscopy method according to claim 7, wherein the intensity of the excitation light pulses for the predetermined pixel is set so that the total number of measurement intervals in which exactly one fluorescence photon is detected is equal to the total number of measurement intervals in which no fluorescence photon is detected.

9. The fluorescence lifetime imaging microscopy method according to claim 1, wherein:
a plurality of interval segments are defined within the respective measurement interval;
the determination as to whether more than the predefined number of fluorescence photons has been detected within the measurement interval is carried out separately for each of these interval segments; and
a respective one of the interval segments for the step of determining the at least one value characterizing the fluorescence decay behavior is discarded based on more than the predefined number of fluorescence photons having been detected within the respective interval segment.

10. The fluorescence lifetime imaging microscopy method according to claim 9, wherein a value characterizing the fluorescence decay behavior of an entire one of the measurement intervals is determined based on values characterizing the fluorescence decay behavior which are determined for each of the interval segments.

11. The fluorescence lifetime imaging microscopy method according to claim 10, wherein the value characterizing the fluorescence decay behavior of the entire one of the measurement intervals is ascertained based on a factor determined from a number of interval segments in which the predefined number of fluorescence photons has been detected and a number of interval segments in which no photon has been detected.

12. The fluorescence lifetime imaging microscopy method according to claim 10, wherein the value characterizing the fluorescence decay behavior of an entire one of the measurement intervals is evaluated based on a model function in which a number of fluorescence photons detected in the interval segments is taken into account.

13. The microscope according to claim 10, wherein the processing unit comprises a display configured to depict setting information.

14. The fluorescence lifetime imaging microscopy method according to claim 9, wherein the interval segments comprise at least two segments, which follow one another within the respective measurement interval with or without time overlap.

15. The fluorescence lifetime imaging microscopy method according to claim 9, wherein the interval segments comprise a first segment formed by the measurement interval and at least one second segment, wherein a beginning of the at least one second segment is delayed with respect to a beginning of the respective measurement interval and wherein an end of the at least one second segment coincides with an end of the respective measurement interval.

16. The fluorescence lifetime imaging microscopy method according to claim 1, being carried out using a confocal scanning microscope or a multiphoton microscope.

17. A microscope for implementing a fluorescence lifetime imaging microscopy method with time-correlated single photon counting, the microscope comprising:
  a light source configured to excite a sample with excitation light pulses to emit fluorescence photons, with a measurement interval being defined between each two successive excitation light pulses,
  a detector configured to detect the fluorescence photons and to generate an analog detector signal representing the detected fluorescence photons, and
  a processor configured to determine detection times at which the fluorescence photons are detected by the detector within the respective measurement intervals based on the detector signal so as to compute at least one value characterizing fluorescence decay behavior based on the detection times, and to perform imaging based on the at least one value,
  wherein the processor is configured to sample the analog detector signal within a respective one of the measurement intervals in a plurality of sampling intervals and to convert the analog detector signal to a sequence of discrete signal values associated with the sampling intervals, and to determine, based on the sequence of discrete signal values associated with the respective measurement interval, whether more than a predefined number of fluorescence photons greater than or equal to 1 has been detected within the respective measurement interval, and
  wherein the processor is configured to discard the respective measurement interval for which it has been determined that more than the predefined number of fluorescence photons has been detected in the step of determining the at least one value characterizing the fluorescence decay behavior.

18. The microscope according to claim 17, wherein the processor comprises an analog-digital converter configured to digitize the analog detector signal.

19. The microscope according to claim 17, wherein the processor comprises a comparator configured to digitize the analog detector signal using a threshold value such that the discrete signal values are each equal to a first binary value or equal to a second binary value.

20. The microscope according to claim 17, further comprising an additional detector configured to detect the excitation light pulses and to generate an analog excitation signal representing the detected excitation light pulses, wherein the processor is configured to sample the analog excitation pulses according to the sampling intervals and to convert the analog excitation pulses into a sequence of discrete excitation signal values associated with the sampling intervals.

21. The microscope according to claim 17, being configured as a confocal scanning microscope or as a multiphoton microscope.

* * * * *